March 7, 1967 H. C. SWIM ETAL Plant Pat. 2,724
ROSE PLANT
Filed Dec. 22, 1965
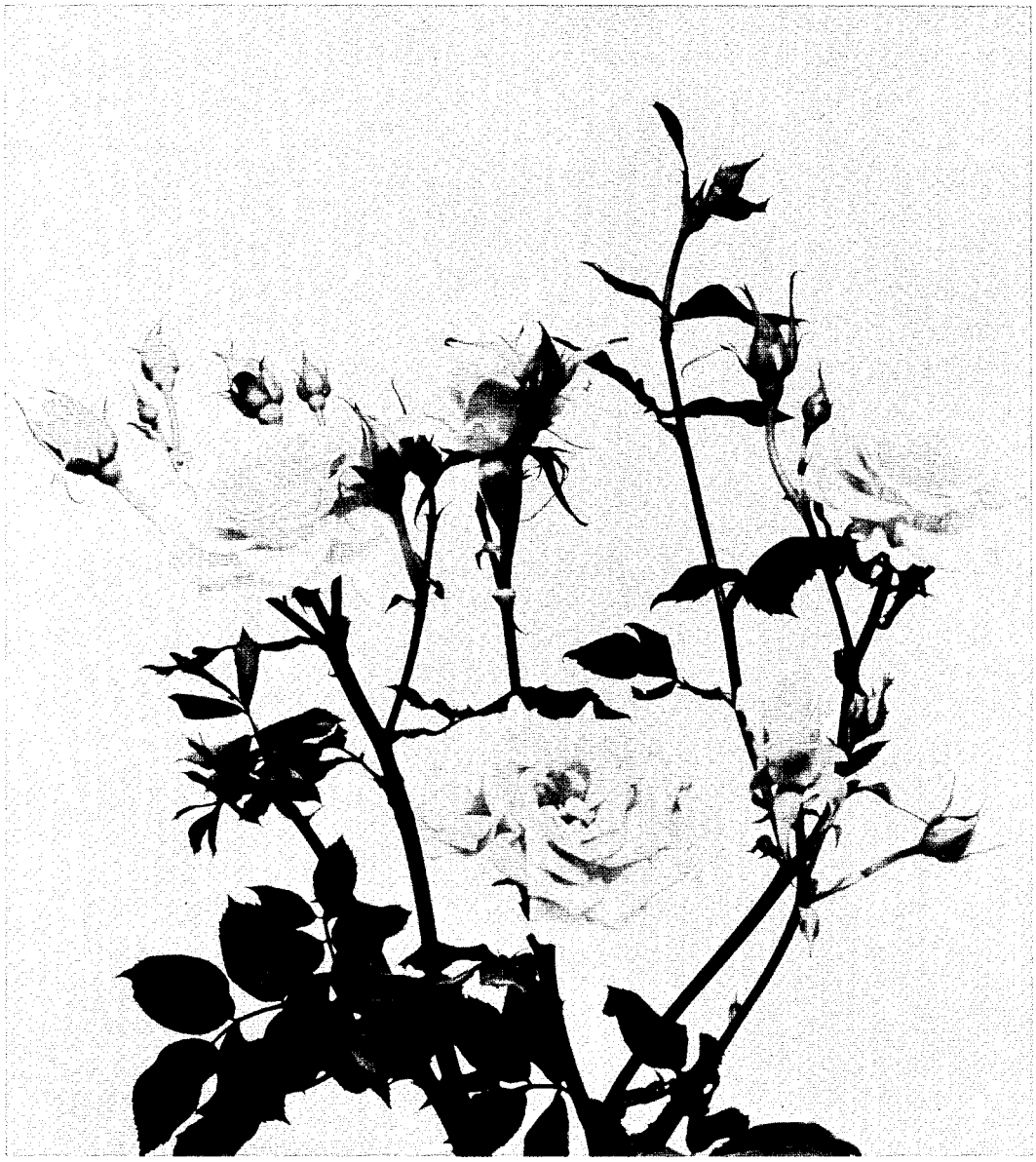
Inventors.
H. C. Swim
O. L. Weeks
By: Robb & Robb
Attorneys.

United States Patent Office

Plant Pat. 2,724
Patented Mar. 7, 1967

2,724
ROSE PLANT

Herbert C. Swim, Ontario, and O. L. Weeks, Chino, Calif., assignors to Swim and Weeks, Chino, Calif., a copartnership Filed Dec. 22, 1965, Ser. No. 515,706
1 Claim. (Cl. Plt.—26)

The present invention relates to a new and distinct variety of rose plant of the floribunda class, which was originated by us by crossing the variety known as "Verona" (Plant Patent No. 2,282) with the variety known as "Escort" (Plant Patent No. 2,436), the former being the seed parent and the latter being the pollen parent.

As the result of this breeding, we have produced a new and improved rose variety which is distinguished from its parents, as well as from all other varieties of which we are aware, as evidenced by the following unique combination of characteristics which are outstanding in the new variety:

(1) Long and relatively straight flower stems as compared with other greenhouse varieties of the floribunda or polyantha classes;

(2) An ability to produce successive crops of flowers without delay under glass and without regard to the season;

(3) A distinctive and attractive flower shape, beginning at the bud stage and progressing to the fully open flower;

(4) Good flower petalage;

(5) A distinctive channelled shape of the flower petals, with the channelling becoming more pronounced as the petals age;

(6) Good flower substance, with consequent good lasting qualities both on the plant and as cut flowers; and (7) A distinctive and attractive medium pink general color tonality of the flowers.

In comparison with its seed parent, "Verona," the channelled shape of the flower petals of the new variety is not typical of the flower petals of the parent variety; the flower petals have substantially greater substance or stiffness which is easily recognized by comparing the "feel" of the petals of the respective varieties; the flowers of the new variety are medium pink in color rather than dainty light pink as in the case of "Verona"; and the flower color of the new variety has substantially less variation in intensity.

As compared with its pollen parent, "Escort," the plant of the new variety is substantially larger at maturity; the channelled shape of the flower petals is not typical of this parent; and the medium pink flower color is substantially lighter than the dark red flower color of "Escort."

Asexual reproduction of our new variety by budding, as performed at Chino, California, shows that the aforementioned characteristics and distinctions come true to form and are established and transmitted through succeeding propagations.

The accompanying drawing shows typical specimens of the vegetative growth and flowers of our new variety in different stages of development and as depicted in color as nearly true as it is reasonably possible to make the same in a color illustration of this character.

The following is a detailed description of our new variety, with color terminology in accordance with the Nickerson Color Fan, published by Munsell Color Company, Incorporated, of Baltimore, Maryland, except where general color terms of ordinary dictionary significance are obvious:

Type: Normal height bush; greenhouse; seedling; for cut flowers.
Class: Floribunda.

Breeding: Seedling.
*Seed parent.*—"Verona."
*Pollen parent.*—"Escort."
Propagation: Holds its distinguishing characteristics through succeeding propagations by budding.

*Flower*

Locality where grown and observed: Ontario, California.
Flowers borne: Usually from 3 to several to stem; in irregular clusters; on stems of medium length and normal strength.
Quantity of bloom: Free, in greenhouse.
Continuity: More or less continuous.
Fragrance: Very slight.
Bud:
*Peduncle.*—Medium length; medium caliper; from bending to erect; with numerous stipitate glands. Color—light green.
*Before calyx breaks.*—Size—large for class. Form—medium length; ovoid; with a conspicuous neck; with foliaceous appendages on the surface of the bud; rarely with foliaceous parts extending beyond the tip of the bud.
*As calyx breaks.*—Color—prominant area at base between Light Yellow Green, Plate 7.5GY 9/4 to Bright Yellow Green, Plate 5GY 8/8, progressively blending with increasing amounts of pink to attain Strong Purplish-Pink, Plate 10RP 5/12 at apex.
*As first petal opens.*—Size—large for class. Form—long; from pointed to urn-shaped. Color: outside—prominent area of greenish-white at base, with strong influence of greenish-white extending up midrib almost to apex, elsewhere blending quickly into between Moderate Pink, Plate 10RP 8/5 and Strong Pink, Plate 10RP 7/8, with latter color dominant at margins; inside—about ⅓ of petal at base near white, succeeding abruptly with pink shades between Deep Purplish-Pink, Plate 7.5RP 6/12 and Strong Purplish-Pink, Plate 7.5RP 7/10, with the latter color dominant at margins.
*Opening.*—Opens up well.
Bloom:
*Size (when fully open).*—Medium for class; usually from 2½ inches to 2¾ inches.
*Petalage.*—Double, but stamens not hidden; from 28 to 40 petals; arranged regularly.
*Form.*—High-centered at first, but becoming more or less flat; petals being at first loosely rolled outward and remaining loosely rolled outward at maturity.
Petals:
*Texture.*—Thick.
*Appearance.*—Inside—satiny. Outside—shiny and crepe-like.
*Shape.*—All petals guttered or channelled, especially with age. Outside—broader than long, with apex acute. Intermediate—broadly obovate, with apex acute. Inside—obovate, with apex acute.

This description of a newly opened flower was made from a rose grown outdoors during the month of November at Ontario, California:

*Color.*—Outer petal: outside surface—white, tinged slightly green, at base for about ⅓ of petal, blending irregularly with pink at first, but becoming a fairly uniform color near Strong Purplish-Pink, Plate 7.5RP 7/10 at margins; inside surface—white, tinged with green, at base for about ¼ of petal, somewhat abruptly becoming between Strong Purplish-Pink, Plate 7.5RP 7/10 and Deep Purplish-Pink, Plate 7.5RP 6/12, with whitish color at base sometimes following midrib and adjacent veins, irregularly and briefly. Intermediate petal: outside surface—white, with very slight greenish tinge, at base for about ¼ of petal, blending or changing rapidly to near Strong Purplish Pink, Plate 7.5RP 7/10; inside surface—near white for about ¼ of petal at base, rapidly blending or changing to near Strong Purplish-Pink, Plate 7.5RP 7/10, with deeper pink markings on veins near Deep Purplish-Pink, Plate 7.5RP 6/12. Inner petal: outside surface — near white for about ¼ of petal at base, sometimes extending irregularly upward along midrib, but merging rapidly elsewhere to between Strong Purplish-Pink, Plate 7.5RP 7/10 and Deep Purplish-Pink, Plate 7.5RP 6/12, and being nearer the latter at margins; inside surface—near white for about ⅕ of petal at base, blending rapidly to near Deep Purplish-Pink, Plate 7.5RP 6/12.

This description was made from a rose that was open for three days indoors during the month of November at Ontario, California:

*Color.*—Outer petal: outside surface—near white for about ⅓ of petal at base, with greenish tinge about midrib, and with remainder ranging from Light Purplish-Pink, Plate 7.5RP 8/5 to near Strong Purplish-Pink, Plate 7.5RP 7/10 at or near margins; inside surface—near white for about ¼ of petal around point of attachment, with remainder ranging from Deep Purplish-Pink, Plate 7.5RP 6/12 through Strong Purplish-Pink, Plate 7.5RP 7/10 to Light Purplish-Pink, Plate 7.5RP 8/5, and with the latter color dominant at apex. Inner petal: outside surface—near white for about ¼ of petal around point of attachment, with remainder near Strong Purplish-Pink, Plate 7.5RP 7/10, except where this blends with the white influence from base where the color becomes closer to Light Purplish-Pink, Plate 7.5RP 8/5; inside surface—near white for about ¼ of petal around point of attachment, with remainder generally between Deep Purplish-Pink, Plate 7.5RP 6/12 and Strong Purplish-Pink, Plate 7.5RP 7/10.

*General color effect.*—Newly opened flower—near Deep Purplish-Pink, Plate 7.5RP 6/12. Three days open—near Strong Purplish-Pink, Plate 7.5RP 7/10.

*Behavior.*—Drop off cleanly.

*Flower longevity.*—On bush in garden—8 days in November. Cut roses grown outdoors and kept at livingroom temperatures—8 days in November.

*Reproductive organs*

Stamens: From medium number to many; arranged more or less regularly about pistils.

Filaments: Long; most with anthers. Color—white.

Anthers: Small; all open approximately at once. Color—white.

Pollen: Color—gold.

Pistils: Many.

Styles: Uneven; from short to medium length; bunched and slightly depressed.

Stigma: Color—whitish-yellow.

Ovaries: Most enclosed in, but some protruding from calyx.

Hips: Nearly round; walls thick and fleshy. Color—yellow-orange.

Sepals: Falling before hips mature.

Seeds: From few to many; small.

*Plant*

Foliage:

*Leaves.*—Compound of 3–5 leaflets; normal quantity; from medium size to large; moderately heavy; leathery; semi-glossy.

*Leaflets.*—Shape—ovoid. Apex—acute. Base—round on terminals and nearly round on laterals. Margin—generally simply serrate.

*Color.*—Mature: upper surface—dark green; under surface—normal grey-green. Young: upper surface—dark green, with some reddish purple overlay; under surface—grey-green, with irregular overlay of reddish-purple on midrib and many veins and in some interstices.

*Rachis (the supporting stem of the compound leaf).*—Medium weight. Upper side—grooved; lined with moderate quantity of stipitate glands. Under side—sparsely prickly; occasionally with 1 or 2 prickles.

*Stipules.*—From short to medium length; narrow; with medium length points turning out at an angle of less than 45°.

*Disease resistance.*—From about average to slightly better than average resistance to powdery mildew, as determined by comparison with many other varieties grown under comparable conditions at Ontario, California.

Growth:

*Habit.*—Medium height; bushy; somewhat spreading; much-branched.

*Growth.*—Vigorous.

*Canes.*—Medium caliper.

*Main stems.* — Color — dull grey-greeen. Large prickles—several; medium length; straight; with short, elliptical base; color—grey-brown. Small prickles—color—grey-brown. Hairs—none.

*Branches.*—Color—moderately bright green. Large prickles—several; medium length; straight; with short, elliptical base; color — brown. Small prickles—few; color—brown. Hairs—none.

*New shoots.* — Color — reddish-purple. Large prickles—few; medium length; straight; with short, elliptical base; color—reddish-purple, with pale green tips. Small prickles—from none to very few; color—reddish-purple. Hairs—none.

We claim:

A new and distinct variety of rose plant of the floribunda class, substantially as herein shown and described, characterized particularly as to novelty by the unique combination of long and relatively straight flower stems as compared with other greenhouse varieties of the floribunda or polyantha classes, an ability to produce successive crops of flowers without delay under glass and without regard to the season, a distinctive and attractive flower shape beginning at the bud stage and progressing to the fully open flower, good flower petalage, a distinctive channelled shape of the flower petals which becomes more pronounced as the petals age, good flower substance, with consequent good lasting qualities both on the plant and as cut flowers, and a distinctive and attractive medium pink general color tonality of the flowers.

No references cited.

ABRAHAM G. STONE, *Primary Examiner.*

ROBERT E. BAGWILL, *Examiner.*